United States Patent
Mackler (10) Patent No.: US 9,248,154 B2
(45) Date of Patent: Feb. 2, 2016

(54) METHODS AND COMPOSITIONS FOR TREATMENT OF URINIARY TRACT INFECTIONS

(71) Applicant: POM Wonderful LLC, Los Angeles, CA (US)

(72) Inventor: Ari Mackler, Los Angeles, CA (US)

(73) Assignee: POM Wonderful, LLC, Los Angeles, CA (US)

( * ) Notice: Subject to any disclaimer, the term of this patent is extended or adjusted under 35 U.S.C. 154(b) by 72 days.

(21) Appl. No.: 13/935,421

(22) Filed: Jul. 3, 2013

(65) Prior Publication Data

US 2014/0010871 A1    Jan. 9, 2014

Related U.S. Application Data

(60) Provisional application No. 61/668,927, filed on Jul. 6, 2012.

(51) Int. Cl.
*A61K 36/45* (2006.01)
*A61K 36/185* (2006.01)

(52) U.S. Cl.
CPC .............. *A61K 36/45* (2013.01); *A61K 36/185* (2013.01)

(58) Field of Classification Search
CPC ............................ A61K 36/45; A61K 36/185
See application file for complete search history.

(56) References Cited

U.S. PATENT DOCUMENTS

| 6,231,866 B1 * | 5/2001 | Mann ............................ 424/732 |
| 2004/0013710 A1 * | 1/2004 | Howell ......................... 424/442 |
| 2011/0280851 A1 * | 11/2011 | Herzlinger et al. .......... 424/94.1 |

OTHER PUBLICATIONS

Giada De Laurentiis. "Pomegranate and Cranberry Bellinis." Reprinted from Giada's Kitchen: New Italian Favorites (2008), in the Nov. 2008 issue of O. The Oprah Magazine.*
http://goldbook.iupac.org (2006-) created by M. Nic. J. Jiral. B. Kosata; updates compiled by A. Jenkins. ISBN 0-9678550-9-8. doi: 10.1351/goldbook.E02297 (accessed May 23, 2015).*
http://goldbook.iupac.org (2006-) created by M. Nic. J. Jiral. B. Kosata; updates compiled by A. Jenkins. ISBN 0-9678550-9-8. doi: 10.1351/goldbook.E02296 (accessed May 23, 2015).*

* cited by examiner

*Primary Examiner* — Bethany Barham
*Assistant Examiner* — Peter Anthopolos
(74) *Attorney, Agent, or Firm* — Cotman IP Law Group, PLC (57) ABSTRACT

A composition for treatment of urinary tract infection derived primarily from pomegranate and cranberry fruit components is disclosed. The composition may be derived from juices, concentrates, liquid extracts, or powdered extracts, e.g. dehydrated pomegranate juice, of pomegranate and cranberry fruits. The concentration of each of the component (i.e. pomegranate product and cranberry product) in the composition is set such as to achieve optimum synergistic effects by increasing urinary tract anti-adhesion activity.

12 Claims, 4 Drawing Sheets

METHODS AND COMPOSITIONS FOR TREATMENT OF URINIARY TRACT INFECTIONS

CROSS-REFERENCE TO RELATED APPLICATIONS

The present application claims the benefit of U.S. Provisional Application Ser. No. 61/668,927, filed on Jul. 6, 2012, the specification of which is herein incorporated by reference for completeness of disclosure.

BACKGROUND OF THE INVENTION

1. Field of the Invention

Embodiments of the invention described herein pertain to the field of medical and nutritional compositions. More particularly, but not by way of limitation, one or more embodiments of the invention comprises methods and pomegranate compositions for treatment of urinary tract infections.

2. Description of the Related Art

Urinary tract infections (UTIs) are a widespread problem. Considerable morbidity, multiple antibiotic treatments, and costs result from its common recurrence. Regretfully, uropathogenic *Escherichia coli* (UPEC), the major pathogen involved in these infections, has become increasingly resistant to β-lactams and fluoroquinolones. Evidence has suggested that consumption of cranberries (*Vaccinium macrocarpon* Ait.) and cranberry juice can be used to help prevent UTI. Consumption of cranberry may prevent adhesion of *E. coli* strains to the uroepithelium thus interfering with this a critical first step in the infection process. Of note, cranberry's effect can be seen with multidrug resistant bacterial strains as well. Data suggests that cranberry's proanthocyanidins (PACs), specifically the unusually condensed tannins with A-type linkages, inhibit *E. coli* (primarily P-fimbriated) adhesion to uroepithelial cells in vitro (Liu Y et al.: Role of cranberry juice on molecular-scale surface characteristics and adhesion behavior of *Escherichia coli*. Biotechnol Bioeng 2006, 93:297.305; Howell A B, et al.: Inhibition of adherence of P fimbriated *Escherichia coli* to uroepithelial-cell surfaces by proanthocyanidin extracts from cranberries. N Engl J Med 1998, 339:1085.1086; Foo L Y et al.: A-type proanthocyanidin trimers from cranberry that inhibit adherence of uropathogenic P-fimbriated *Escherichia coli*. J Nat Prod 2000, 63:1225.1228; Gupta K et al.: Cranberry products inhibit adherence of uropathogenic *Escherichia coli* to primary cultured bladder and vaginal epithelial cells. J Urol 2007, 177: 2357.2360), and ex vivo (Howell A B et al.: In vivo evidence that cranberry proanthocyanidins inhibit adherence of P-fimbriated *E. coli* bacteria to uroepithelial cells. FASEB J 2001, 15: A284; Howell A B, et al.: Dosage effect on uropathogenic *Escherichia coli* anti-adhesion activity ("AAA") in urine following consumption of cranberry powder standardized for proanthocyanidin content: a multicentric randomized double blind study. BMC Infect Dis 2010, 10:94.

Anecdotal evidence suggests that consumption of pomegranates may be beneficial for urinary tract health. Pomegranates contain hydrolyzable tannins which have been shown to have a number of health promoting properties. The role of pomegranate extracts as anti-microbial compounds has also been explored (Chulasiri, M. et al. 1995. Mahidol. Iniv. J. Pharm. Sci. 22:1-159; 25. Chulasiri, M. 1997. Thai. J. Phytopharm. 4:25-30; 26. Stewart, G. S. et al. 1998. J. Appl. Microbiol. 84:777-783; Segura, J. J. et al. 1990. Arch. Invest. Med. 21:235-239). However, in each case, the pomegranate extract was shown only to inhibit bacterial growth, not to inhibit bacterial adherence to surfaces.

U.S. patent application Ser. No. 10/332,425 discloses hydrolyzable tannin extracts from plants which acts to prevent bacterial adherence to surfaces. Hydrolyzable tannin extracts from plants, in particular pomegranate and persimmon, were shown to have activity to inhibit adhesion of bacteria to surfaces.

BRIEF SUMMARY OF THE INVENTION

One or more embodiments of the invention comprise methods and compositions for treatment of urinary tract infections.

One or more embodiments of the methods and compositions for treatment of urinary tract infection disclosed herein are directed to a composition that includes pomegranate-derived components and cranberry-derived components. The composition may be derived from one or more juices, liquid extracts ("shot"), or powdered extracts, etc.

The composition in one or more embodiments of the present invention may be administered orally or parenterally employing liquid form preparations. The composition may be administered orally, in appropriate dosage units in a pharmaceutically acceptable carrier or excipient. Thus, the composition may be formulated into solid or liquid preparations, such as capsules, pills, tablets, powders, solutions, suspension, or emulsions and prepared according to methods known in the art for the manufacture of such compositions. The solid unit dosage configuration may be in form of a hard or soft shelled gelatin capsule containing the active components and a suitable carrier or excipient.

One or more embodiments of methods and compositions for treatment of urinary tract infection disclosed herein are directed to a liquid product comprising a liquid pomegranate product and a liquid cranberry product. The liquid cranberry product may be a cranberry juice, a cranberry juice concentrate, or any other liquid derived from cranberry.

One or more embodiments of methods and compositions for treatment of urinary tract infection disclosed herein are directed to a dry product comprising a dry pomegranate product and a dry cranberry product. The dry pomegranate product may be a pomegranate powder extract, a dehydrated pomegranate juice, or any other dry composition derived from pomegranate. The dry cranberry product may be a cranberry powder extract, a dehydrated cranberry juice, or any other dry composition derived from cranberry.

One or more embodiments of the methods and compositions disclosed herein are directed to the prevention or treatment of urinary tract infection.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

A method and compositions for treatment of urinary tract infection will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. Furthermore, although steps or processes are set forth in an example order to provide an understanding of one or more systems and methods, the exemplary order is not meant to be limiting. One of ordinary skill in the art would recognize that the steps or processes may be performed in a different order, and that one or more steps or processes may be performed simultaneously or in multiple process flows without departing from the spirit or the scope of the claimed invention. In other instances, specific features, quantities, or measurements well known to those of ordinary skill in the art have not been described in detail so as not to obscure the invention. It should be noted that although examples of the invention are set forth herein, the claims, and the full scope of any equivalents, are what define the invention.

One or more embodiments of the methods and compositions for treatment of urinary tract infection disclosed herein are directed to a composition derived primarily from pomegranate and cranberry fruit components. The composition may be derived from juices, concentrates, liquid extracts ("shot"), or powdered extracts, e.g. dehydrated pomegranate juice ("Pomegranate Juice Powder" or "Pomegranate Juice Crystal"), of pomegranate and cranberry fruits. The concentration of each of the component (i.e. pomegranate product and cranberry product) in the composition is set such as to achieve optimum synergistic effects by increasing urinary tract anti-adhesion activity.

In one or more embodiments, the composition comprises polyphenolic content of approximately 15% cranberry fruit component and approximately 85% pomegranate fruit component. Those of skill in the art would appreciate that the concentrations of the active components (e.g. pomegranate and cranberry) may vary within certain ranges so long as the synergistic effect of increasing urinary tract anti-adhesion activity is achieved. For instance, the concentration of the polyphenolic content of the pomegranate fruit component may vary between 50% and 90% with the corresponding concentration of the polyphenolic content of cranberry fruit component of between 50% and 10%. The net sum of the concentrations should comprise approximately 100% of the active components of the composition. For instance, the concentrations could be approximately 50% pomegranate and approximately 50% cranberry, approximately 75% pomegranate and approximately 25% cranberry, approximately 80% pomegranate and approximately 20% cranberry, approximately 90% pomegranate and approximately 10% cranberry, etc.

The pomegranate fruit component may be obtained from one or more of the methods described in, for example, U.S. Pat. No. 7,611,738, entitled "Processes for extracting phytochemicals from pomegranate solids and compositions and methods of use thereof," filed on May 24, 2005. The specification of which is herein incorporated by reference in its entirety. The pomegranate fruit component may also be obtained from any other method known in the art. The pomegranate-derived component contains ellagitannins, oligomeric hydrolyzable tannins and anthocyanins.

The cranberry fruit component may be derived from any method known in the art and contains hydroxycinnamic acids, anthocyanins, flavonols and proanthocyanidins that are typical for cranberry juice.

One or more embodiments of the composition of the present invention for treating urinary tract infections are directed to a dosage unit between approximately 25 mg and 2000 mg. For instance the dosage could be in units of 25 mg, 50 mg, 100 mg, 150 mg, 200 mg, 250 mg, 300 mg, 400 mg, 500 mg, 750 mg, 1000 mg, 1,500 mg, 1,788 mg, etc.

The composition may also include other components such as caffeine and sugar, for instance. The compositions may include one or more sugars derived from pomegranates. Sugars may be useful to add to the composition as they have the ability to reduce bacterial adhesion in the urinary tract. Pomegranate sugar is the clarified, 65Brix, water soluble fraction which has an acid, sugar, and mineral profile derived from the pomegranate by-product. These sugars have integrated pomegranate polyphenols.

In one or more embodiments, the sugar may include a complex sugar elution derived from pomegranate via polymer column extraction, for example. The sugars may include compound sugars and sugar-polyphenol compounds derived from pomegranates.

In one or more embodiments, the composition may be administered orally or parenterally employing liquid from preparations containing the composition. The composition may be administered orally, in appropriate dosage units in a pharmaceutically acceptable carrier or excipient. Thus, the composition may be formulated into solid or liquid preparations, such as capsules, pills, tablets, powders, solutions, suspension, or emulsions and prepared according to methods known in the art. The solid unit dosage configuration may be in the form of a hard or soft shelled gelatin capsule containing the active components of the composition and a suitable carrier or excipient.

One or more embodiments of the composition for treatment of urinary tract infection disclosed herein are directed to a liquid product comprising a liquid pomegranate product and a liquid cranberry product. The liquid pomegranate product may be a pomegranate juice, a pomegranate juice concentrate, or any other liquid derived from pomegranate. The liquid cranberry product may be a cranberry juice, a cranberry juice concentrate, or any other liquid derived from cranberry. In a preferred embodiment, the active components (or portions) of the composition of the present invention comprises approximately 85% pomegranate juice concentrate (PJC) and approximately 15% cranberry juice concentrate (CJC).

One or more embodiments of the composition for treatment of urinary tract infection disclosed herein are directed to a dry product comprising a dry pomegranate product and a dry cranberry product. In a preferred embodiment, the composition comprises polyphenolic content of approximately 15% cranberry fruit component and approximately 85% pomegranate fruit component. The dry pomegranate component may be a pomegranate powder extract, a pomegranate powder, dehydrated pomegranate juice, or any other dry composition derived from pomegranate. The dry cranberry component may be a cranberry powder extract, a cranberry powder, dehydrated cranberry juice, or any other dry composition derived from cranberry. Those of skill in the art would appreciate that other polyphenolic content percentages (or ratios) are also contemplated so long as the synergistic effects of significantly increasing urinary tract anti-adhesion activity is achieved beyond that provided by either component alone. That is, it should be understood that other variations polyphenolic content percentages are contemplated thereof so long as effectiveness remains and treatment of urinary tract infections is achieved.

The compositions may be administered orally, in appropriate dosage units of the extract in a pharmaceutically acceptable carrier or excipient. Thus, the compositions may be formulated into solid or liquid preparations, such as capsules, pills, tablets, powders, solutions, suspension, or emulsions and prepared according to methods known in the art for the manufacture of such compositions. The solid unit dosage forms may be in form of a hard or soft shelled gelatin capsule containing the active components of the composition and a suitable carrier or excipient.

The dosage used in the embodiments may be applied in any suitable form, such as bars, pills, capsules, gels, liquid, etc. A dosage unit may comprise a powder, solid or semisolid form, and more acceptable in a dosage form includes without limitation, caplets, capsules, gelatin coated capsule, granules, microparticles, microspheres, pills, powder, tablets, and other solid or semisolid formulations. In one or more embodiments, a daily dosage of the prepared polyphenol can include one or more pills, tablets or other dosage forms. Concentrated liquid forms are also contemplated and may be made by mixing in the powder and other forms of the components (e.g. liquid) described herein. Alternatively or in addition the liquid concentrate itself can be produced from byproducts of the juice production process.

Pomegranate Product

Pomegranates contain hydrolyzable tannins which have been shown to have a number of health promoting properties, but they have not been associated with prevention of bacterial adhesion. Research has demonstrated that pomegranate prevents in vitro P-type *E. coli* adhesion, and also Type 1 bacterial adhesion. The activity may be due not only to the tannins, but other components in the product.

Pomegranate products (e.g. pomegranate juice cocktail, pomegranate extract such as POMx™, etc) contain ellagitannins, oligomeric hydrolyzable tannins and anthocyanins. The ellagitannins include punicalin and punicalagin along with dimeric and trimeric ellagitannins.

Cranberry Product

The proanthocyanidins (PACs) in cranberry prevent adhesion of P-type *E. coli*. There is also in vitro activity from the sugar (fructose) in cranberry against Type 1 *E. coli*, but it is not likely to be effective in vivo, as sugars are metabolized and are not normally found in urine. The cranberry component contains hydroxycinnamic acids, anthocyanins, flavonols and proanthocyanidins that are typical for cranberry juice. The tannins in cranberry comprise "A-type" proanthocyanidin oligomers from the dimer to decamer. The active anti-adhesion compounds in cranberries have been identified as unusual types of proanthocyanidin, or condensed tannin with double A-type linkages.

Composition of Pomegranate and Cranberry ("POMCran")

As discussed above, one embodiment of the composition of the present invention comprises a blend with polyphenolic content consistent with approximately 85% Pomegranate Juice Concentrate and approximately 15% Cranberry Juice Concentrate. The Pomegranate Cranberry Blend has total polyphenol components contributed by both the Pomegranate concentrate (hydrolysable tannins) and Cranberry concentrate (proanthocyanidins). The anthocyanins in the pomegranate cranberry blend are contributed by the both Pomegranate concentrate and cranberry concentrate in a manner that is consistent with the ratio of pomegranate/cranberry blend (e.g. 85:15).

The examples below present results of studies to characterize the anti-adhesion activity effects of the pomegranate product (e.g. pomegranate juice concentrate), cranberry product (e.g. cranberry juice concentrate), and the blend of pomegranate and cranberry in accordance with an embodiment of the present invention. Of particular interest, is the synergistic effect between the pomegranate and cranberry products when blended together to form the composition of the present invention. The mechanism of action through chromatographic isolation and molecular characterization of the structural complexes formed by the tannins in the pomegranate and cranberry juices is investigated in vitro and in vivo.

Example 1

Study of Bacterial AAA Effects

The ex vivo urinary anti-adhesion activity following ingestion of pomegranate cranberry juice (POMCran™) was investigated to determine if there is a synergistic effect of the two juices together. The effect was compared to Cranberry Juice Cocktail-Light and POMx capsules. Chromatographic isolation and molecular characterization are used to evaluate whether the structural complexes formed by the tannins in the pomegranate and cranberry juices are responsible for the change in anti-adhesion activity.

The study involves detecting bacterial AAA in POMCran juice and how it compares to 27% Cranberry Juice Cocktail-Light and POMx and to determine if there is a synergistic in vivo effect in POMCran when both cranberry PACs and pomegranate hydrolyzable tannins are contributed by both products.

Twenty (20) healthy middle-aged volunteers (10 men and 10 women) were used in the study to determine both the uropathogenic bacterial (P-type and Type 1 *E. coli*) AAA in human urine following consumption of three different product treatments comprising: 1) 8 oz POMCran juice; 2) 8 oz 27% Cranberry Juice Cocktail-Light; and 3) one 1000-mg POMx capsule. The results were measured over a 60-hour time frame with the product consumed at the beginning of the test period only. The study also included determining if there is a difference in the response of men vs. women.

The purpose of this study was to determine the bacterial AAA and basic pharmacodynamics of POMCran juice, which is a mixture of approximately 15% cranberry and approximately 85% pomegranate, and compare it to the activities and pharmacodynamics of 27% Cranberry Juice Cocktail-Light (CJC-Light) and POMx capsule (or other 100% pomegranate product).

Dietary restrictions—participants (10 women and 10 men, between the ages of 25 and 60) refrained from consuming all cranberry, blueberry, pomegranate, grape, chocolate and other high-flavonoid products for a 3-day wash out period prior to consuming test products and throughout the testing period. The study was conducted as follows:

3-day wash out period prior to consuming test products and throughout test period;

On urine collection days, additional fluid consumption standardized for volunteers to 240 mL every 3 hours to avoid dilution of urine samples and allow for detection of AAA, if present;

On test days, products were administered in the morning;
Urine (approximately 25 ml) was collected (clean-catch) by each participant prior to product consumption and at 6, 12, 24, 36, 48 and 60 hours following product consumption;
Urine was centrifuged, filtered (0.45 micron filter) and immediately frozen at −20 C.

To begin, reference urine samples were taken from all 20 participants prior to consumption of treatment products. Treatment 1 (i.e. 8-oz POMCran juice) was administered in the morning to the 20 healthy middle-aged participants over a 2-day period. On the morning of day 2, urines were collected prior to product consumption and after product consumption at intervals of 6, 12, 24, 36, 48 and 60 hours and each collection was immediately frozen at −20 C. After a 3-day wash-out period, treatment 2 (8-oz 27% Cranberry Juice Cocktail-Light) were administered, as stated above, and urines collected and frozen at −20 C. After an additional 3-day wash-out period, treatment 3 (one 1000 mg POMx capsule) was administered, urines collected and frozen, as stated above.

Thawed urines were tested full-strength for bacterial AAA utilizing both mannose resistant and mannose sensitive hemagglutination assays specific for P-fimbriated and Type 1-fimbriated *E. coli*, respectively. The minimum inhibitory concentration (MIC) that detects 50% anti-adhesion activity in each sample was recorded as the endpoint for each assay.

Results

No anti-adhesion activity was detected in urines prior to consumption of products. Urinary pH averaged 6.2, eliminating a bacteriostatic effect.

Figure 1A:
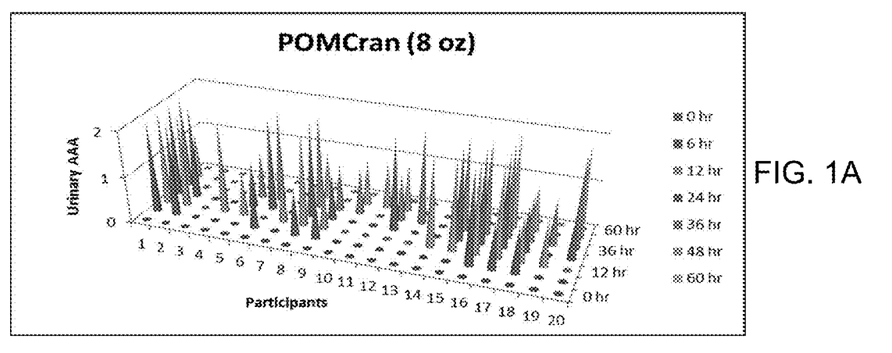
FIG. 1A is a graphical illustration of observed urinary AAA against P-fimbriated *E. coli* for each participant over each collection time period for the 8 oz POMCran blend.
Figure 1B:
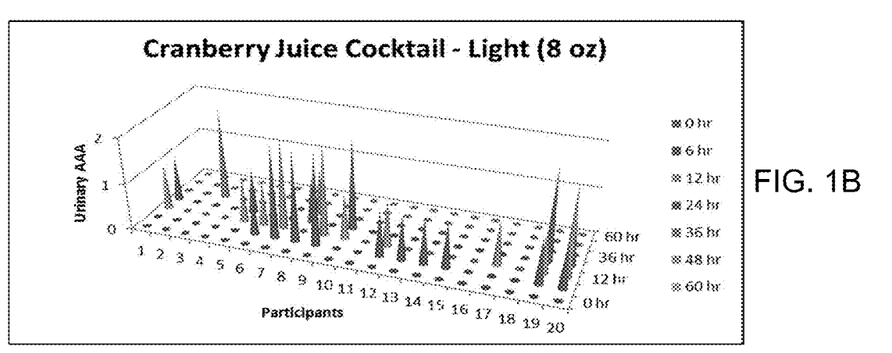
FIG. 1B is a graphical illustration of observed urinary AAA against P-fimbriated *E. coli* for each participant over each collection time period for the 8 oz Cranberry Juice Cocktail.
Figure 1C:
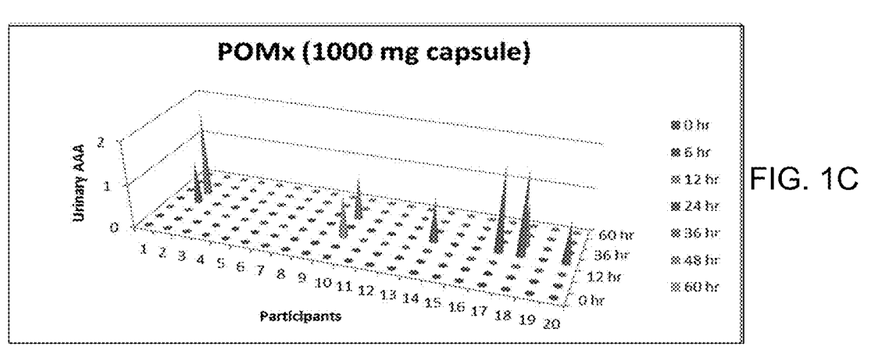
FIG. 1C is a graphical illustration of observed urinary AAA against P-fimbriated *E. coli* for each participant over each collection time period for 1000 mg POMx product.

FIGS. 1A-C are graphical illustrations of observed urinary AAA against P-fimbriated *E. coli* for each participant over each collection time period. The raw data is also presented in Table 1. Summing all observed urinary AAA against P-type *E. coli* recorded for all participants over every time period yielded 84 out of a possible 280 for POMCran, 37 out of a possible 280 for CJC-Light, and 12 out of a possible 280 for POMx. Overall, POMCran (FIG. 1A) had significantly greater ($p<0.05$) urinary AAA against P-type *E. coli* than both the CJC-Light (FIG. 1B) and POMx (FIG. 1C), suggesting a possible synergistic effect of the tannins from the different products forming the blend (i.e. POMCran). The CJC-Light treatment had significantly greater AAA than the POMx ($p<0.05$).

TABLE 1

AAA of Products against P-fimbriated *E. coli*.

| Participant | Composition | 0 hr | 6 hr | 12 hr | 24 hr | 36 hr | 48 hr | 60 hr |
|---|---|---|---|---|---|---|---|---|
| 1F | POMCran | 0 | 2 | 2 | 2 | 2 | 1 | 0 |
| 2F | POMCran | 0 | 2 | 2 | 2 | 0 | 0 | 0 |
| 3F | POMCran | 0 | 0 | 0 | 0 | 0 | 0 | 0 |
| 4F | POMCran | 0 | 0 | 2 | 0 | 0 | 0 | 0 |
| 5F | POMCran | 0 | 0 | 1 | 1 | 1 | 0 | 0 |
| 6F | POMCran | 0 | 1 | 0 | 2 | 2 | 0 | 0 |
| 7F | POMCran | 0 | 0 | 1 | 0 | 0 | 0 | 0 |
| 8F | POMCran | 0 | 1 | 2 | 2 | 2 | 1 | 0 |
| 9F | POMCran | 0 | 1 | 1 | 1 | 1 | 0 | 0 |
| 10F | POMCran | 0 | 0 | 0 | 0 | 1 | 1 | 0 |
| 11M | POMCran | 0 | 0 | 0 | 0 | 0 | 1 | 0 |
| 12M | POMCran | 0 | 0 | 0 | 2 | 1 | 1 | 0 |
| 13M | POMCran | 0 | 0 | 0 | 0 | 2 | 0 | 0 |
| 14M | POMCran | 0 | 0 | 2 | 0 | 0 | 0 | 0 |
| 15M | POMCran | 0 | 0 | 2 | 2 | 2 | 0 | 0 |
| 16M | POMCran | 0 | 2 | 2 | 2 | 2 | 0 | 0 |
| 17M | POMCran | 0 | 1 | 2 | 2 | 2 | 2 | 0 |
| 18M | POMCran | 0 | 1 | 1 | 1 | 1 | 1 | 0 |
| 19M | POMCran | 0 | 0 | 1 | 0 | 1 | 0 | 0 |
| 20M | POMCran | 0 | 0 | 0 | 1 | 2 | 2 | 0 |
| 1F | CJC | 0 | 0 | 1 | 1 | 0 | 0 | 0 |
| 2F | CJC | 0 | 0 | 0 | 0 | 0 | 0 | 0 |
| 3F | CJC | 0 | 0 | 0 | 0 | 2 | 0 | 0 |
| 4F | CJC | 0 | 0 | 0 | 0 | 0 | 0 | 0 |
| 5F | CJC | 0 | 0 | 1 | 1 | 0 | 0 | 0 |
| 6F | CJC | 0 | 1 | 1 | 0 | 0 | 0 | 0 |
| 7F | CJC | 0 | 2 | 2 | 0 | 0 | 0 | 0 |
| 8F | CJC | 0 | 2 | 0 | 1 | 1 | 0 | 0 |
| 9F | CJC | 0 | 2 | 2 | 0 | 0 | 0 | 0 |
| 10F | CJC | 0 | 0 | 1 | 2 | 0 | 0 | 0 |
| 11M | CJC | 0 | 0 | 0 | 0 | 0 | 0 | 0 |
| 12M | CJC | 0 | 1 | 1 | 0 | 0 | 0 | 0 |
| 13M | CJC | 0 | 1 | 0 | 0 | 0 | 0 | 0 |
| 14M | CJC | 0 | 1 | 0 | 0 | 0 | 0 | 0 |
| 15M | CJC | 0 | 1 | 0 | 0 | 0 | 0 | 0 |
| 16M | CJC | 0 | 0 | 0 | 0 | 0 | 0 | 0 |
| 17M | CJC | 0 | 0 | 1 | 0 | 0 | 0 | 0 |
| 18M | CJC | 0 | 0 | 0 | 0 | 0 | 0 | 0 |
| 19M | CJC | 0 | 1 | 1 | 2 | 0 | 0 | 0 |
| 20M | CJC | 0 | 1 | 2 | 1 | 0 | 0 | 0 |
| 1F | POMx | 0 | 0 | 0 | 0 | 0 | 0 | 0 |
| 2F | POMx | 0 | 0 | 0 | 1 | 2 | 0 | 0 |
| 3F | POMx | 0 | 0 | 0 | 0 | 0 | 0 | 0 |
| 4F | POMx | 0 | 0 | 0 | 0 | 0 | 0 | 0 |
| 5F | POMx | 0 | 0 | 0 | 0 | 0 | 0 | 0 |
| 6F | POMx | 0 | 0 | 0 | 0 | 0 | 0 | 0 |
| 7F | POMx | 0 | 0 | 0 | 0 | 0 | 0 | 0 |
| 8F | POMx | 0 | 0 | 0 | 0 | 0 | 0 | 0 |
| 9F | POMx | 0 | 0 | 0 | 0 | 0 | 0 | 0 |
| 10F | POMx | 0 | 0 | 1 | 0 | 1 | 0 | 0 |
| 11M | POMx | 0 | 0 | 0 | 0 | 0 | 0 | 0 |
| 12M | POMx | 0 | 0 | 0 | 0 | 0 | 0 | 0 |
| 13M | POMx | 0 | 0 | 0 | 0 | 0 | 0 | 0 |
| 14M | POMx | 0 | 0 | 0 | 1 | 0 | 0 | 0 |
| 15M | POMx | 0 | 0 | 0 | 0 | 0 | 0 | 0 |
| 16M | POMx | 0 | 0 | 0 | 0 | 0 | 0 | 0 |
| 17M | POMx | 0 | 0 | 0 | 2 | 0 | 0 | 0 |
| 18M | POMx | 0 | 0 | 0 | 2 | 1 | 0 | 0 |

As illustrated in Table 2, there was no urinary AAA against Type-1 *E. coli* detected at any time period for any of the products.

TABLE 2

AAA of Products against Type 1-fimbriated *E. coli*.

| Participant | Composition | 0 hr | 6 hr | 12 hr | 24 hr | 36 hr | 48 hr | 60 hr |
|---|---|---|---|---|---|---|---|---|
| 1F | POMCran | 0 | 0 | 0 | 0 | 0 | 0 | 0 |
| 2F | POMCran | 0 | 0 | 0 | 0 | 0 | 0 | 0 |
| 3F | POMCran | 0 | 0 | 0 | 0 | 0 | 0 | 0 |
| 4F | POMCran | 0 | 0 | 0 | 0 | 0 | 0 | 0 |
| 5F | POMCran | 0 | 0 | 0 | 0 | 0 | 0 | 0 |
| 6F | POMCran | 0 | 0 | 0 | 0 | 0 | 0 | 0 |
| 7F | POMCran | 0 | 0 | 0 | 0 | 0 | 0 | 0 |
| 8F | POMCran | 0 | 0 | 0 | 0 | 0 | 0 | 0 |
| 9F | POMCran | 0 | 0 | 0 | 0 | 0 | 0 | 0 |
| 10F | POMCran | 0 | 0 | 0 | 0 | 0 | 0 | 0 |
| 11M | POMCran | 0 | 0 | 0 | 0 | 0 | 0 | 0 |
| 12M | POMCran | 0 | 0 | 0 | 0 | 0 | 0 | 0 |
| 13M | POMCran | 0 | 0 | 0 | 0 | 0 | 0 | 0 |
| 14M | POMCran | 0 | 0 | 0 | 0 | 0 | 0 | 0 |
| 15M | POMCran | 0 | 0 | 0 | 0 | 0 | 0 | 0 |
| 16M | POMCran | 0 | 0 | 0 | 0 | 0 | 0 | 0 |
| 17M | POMCran | 0 | 0 | 0 | 0 | 0 | 0 | 0 |
| 18M | POMCran | 0 | 0 | 0 | 0 | 0 | 0 | 0 |
| 19M | POMCran | 0 | 0 | 0 | 0 | 0 | 0 | 0 |
| 20M | POMCran | 0 | 0 | 0 | 0 | 0 | 0 | 0 |
| 1F | CJC | 0 | 0 | 0 | 0 | 0 | 0 | 0 |
| 2F | CJC | 0 | 0 | 0 | 0 | 0 | 0 | 0 |

TABLE 2-continued

AAA of Products against Type 1-fimbriated E. coli.

| Participant | Composition | 0 hr | 6 hr | 12 hr | 24 hr | 36 hr | 48 hr | 60 hr |
|---|---|---|---|---|---|---|---|---|
| 3F | CJC | 0 | 0 | 0 | 0 | 0 | 0 | 0 |
| 4F | CJC | 0 | 0 | 0 | 0 | 0 | 0 | 0 |
| 5F | CJC | 0 | 0 | 0 | 0 | 0 | 0 | 0 |
| 6F | CJC | 0 | 0 | 0 | 0 | 0 | 0 | 0 |
| 7F | CJC | 0 | 0 | 0 | 0 | 0 | 0 | 0 |
| 8F | CJC | 0 | 0 | 0 | 0 | 0 | 0 | 0 |
| 9F | CJC | 0 | 0 | 0 | 0 | 0 | 0 | 0 |
| 10F | CJC | 0 | 0 | 0 | 0 | 0 | 0 | 0 |
| 11M | CJC | 0 | 0 | 0 | 0 | 0 | 0 | 0 |
| 12M | CJC | 0 | 0 | 0 | 0 | 0 | 0 | 0 |
| 13M | CJC | 0 | 0 | 0 | 0 | 0 | 0 | 0 |
| 14M | CJC | 0 | 0 | 0 | 0 | 0 | 0 | 0 |
| 15M | CJC | 0 | 0 | 0 | 0 | 0 | 0 | 0 |
| 16M | CJC | 0 | 0 | 0 | 0 | 0 | 0 | 0 |
| 17M | CJC | 0 | 0 | 0 | 0 | 0 | 0 | 0 |
| 18M | CJC | 0 | 0 | 0 | 0 | 0 | 0 | 0 |
| 19M | CJC | 0 | 0 | 0 | 0 | 0 | 0 | 0 |
| 20M | CJC | 0 | 0 | 0 | 0 | 0 | 0 | 0 |
| 1F | POMx | 0 | 0 | 0 | 0 | 0 | 0 | 0 |
| 2F | POMx | 0 | 0 | 0 | 0 | 0 | 0 | 0 |
| 3F | POMx | 0 | 0 | 0 | 0 | 0 | 0 | 0 |
| 4F | POMx | 0 | 0 | 0 | 0 | 0 | 0 | 0 |
| 5F | POMx | 0 | 0 | 0 | 0 | 0 | 0 | 0 |
| 6F | POMx | 0 | 0 | 0 | 0 | 0 | 0 | 0 |
| 7F | POMx | 0 | 0 | 0 | 0 | 0 | 0 | 0 |
| 8F | POMx | 0 | 0 | 0 | 0 | 0 | 0 | 0 |
| 9F | POMx | 0 | 0 | 0 | 0 | 0 | 0 | 0 |
| 10F | POMx | 0 | 0 | 0 | 0 | 0 | 0 | 0 |
| 11M | POMx | 0 | 0 | 0 | 0 | 0 | 0 | 0 |
| 12M | POMx | 0 | 0 | 0 | 0 | 0 | 0 | 0 |
| 13M | POMx | 0 | 0 | 0 | 0 | 0 | 0 | 0 |
| 14M | POMx | 0 | 0 | 0 | 0 | 0 | 0 | 0 |
| 15M | POMx | 0 | 0 | 0 | 0 | 0 | 0 | 0 |
| 16M | POMx | 0 | 0 | 0 | 0 | 0 | 0 | 0 |
| 17M | POMx | 0 | 0 | 0 | 0 | 0 | 0 | 0 |
| 18M | POMx | 0 | 0 | 0 | 0 | 0 | 0 | 0 |
| 19M | POMx | 0 | 0 | 0 | 0 | 0 | 0 | 0 |

Figure 2:
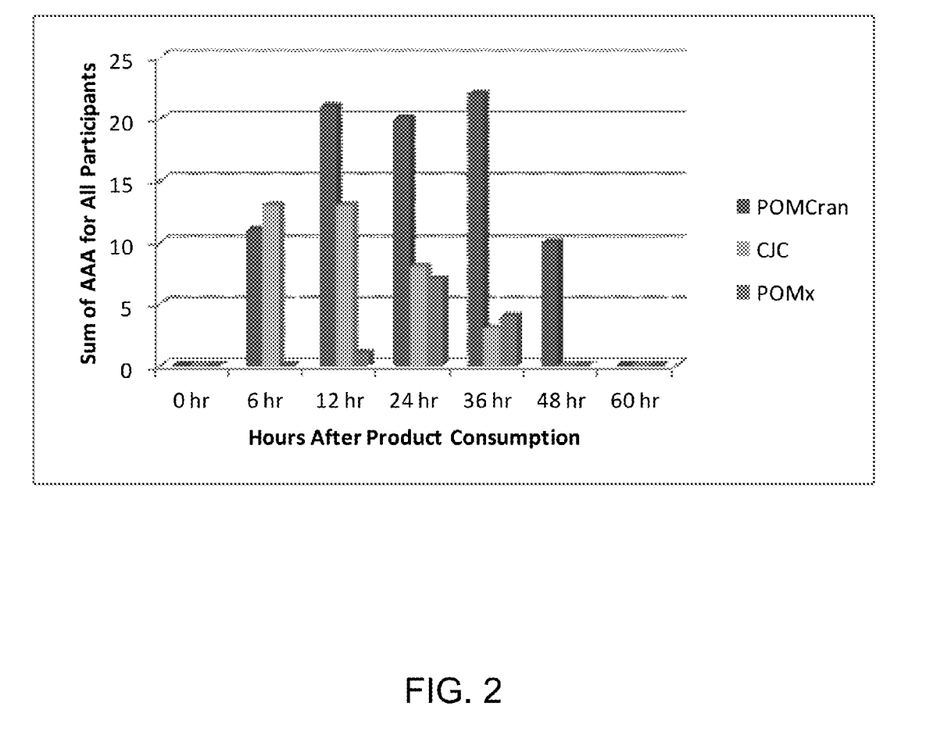
FIG. 2 is a graphical illustration of the distribution of the AAA for all participants at each time period.

FIG. 2 is a graphical illustration of the distribution of the AAA for all participants at each time period. As illustrated, POMCran (first graph) had significantly greater AAA than both CJC-Light (second) and POMx (third) at 12-, 24-, 36-, and 48-hour urine collection periods (p<0.05). This suggests a potential synergistic effect of POMCran at these time periods. At both 36 and 48 hours, the difference in AAA was highly significant (p<0.0002). This indicates that the synergistic effect could be increasing the persistence of the AAA in urine for up to 48 hours. This increase in ex vivo AAA may result in a clinically relevant prevention of urinary tract infections.

There was no significant difference between POMCran and CJC-Light at the 6-hour collection. Thus, POMCran would not be more beneficial than cranberry juice at 6 hours after consumption.

CJC Light had significantly greater AAA than POMx at both the 6- and 12-hour collection times (p<0.05). POMx elicited some activity at 12-, 24-, and 36-hour time points, but the AAA was not statistically significant when compared to the AAA of the other products.

Figure 3:
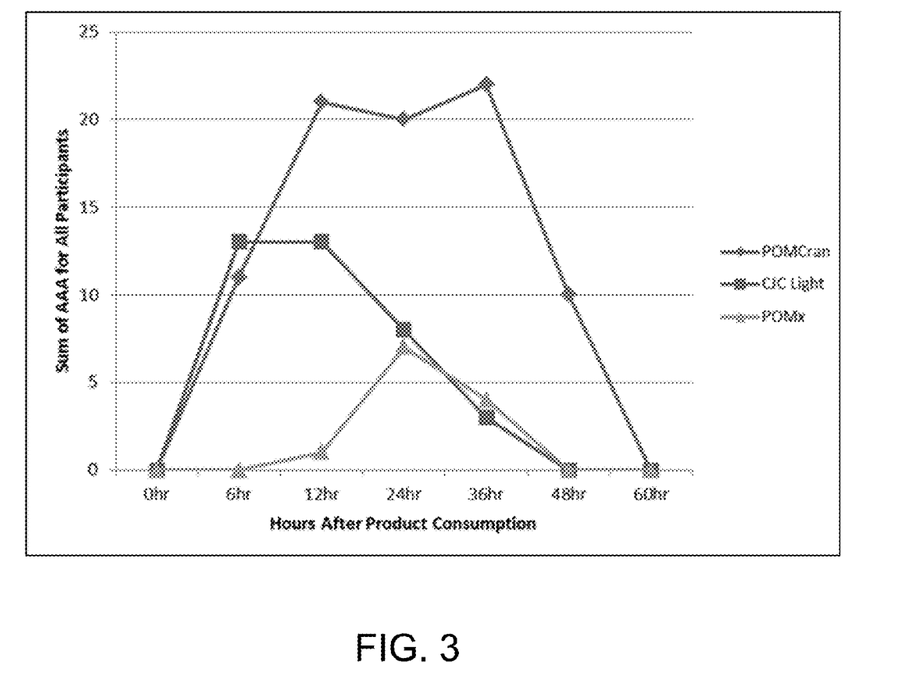
FIG. 3 is a graphical illustration of the comparison of AAA by product at each urine collection time period.

FIG. 3 is a graphical illustration of the comparison of AAA by product at each urine collection time period. As illustrated, the pharmacodynamics pattern of the AAA for POMCran is typically bell-shaped, with significant AAA beginning at 6 hours, peaking and holding between 12 and 36 hours and dropping off at 48 hours (P<0.0001). No activity was detected at 60 hours. These results indicate that the one 8-oz serving of POMCran taken over two days could potentially provide AAA in the urine from 6-48 hours post-consumption.

CJC-Light elicited significant AAA at 6, 12 and 24 hours after consumption (P<0.0001). The AAA peaked early and then declined, shifting the pharmacodynamics curve to the left, compared to POMCran. These results suggest that 8 ounces of CJC-Light taken over two days could provide urinary AAA from 6-24 hours post-consumption.

POMx produced significant AAA at 24 hours post-consumption (p=0.0022). The AAA is pyramid-shaped with a slow increase in activity, which dropped off rapidly. Since there was only significant AAA at a single time-point, POMx may not provide sufficient urinary AAA to maintain urinary tract health.

Figure 4:
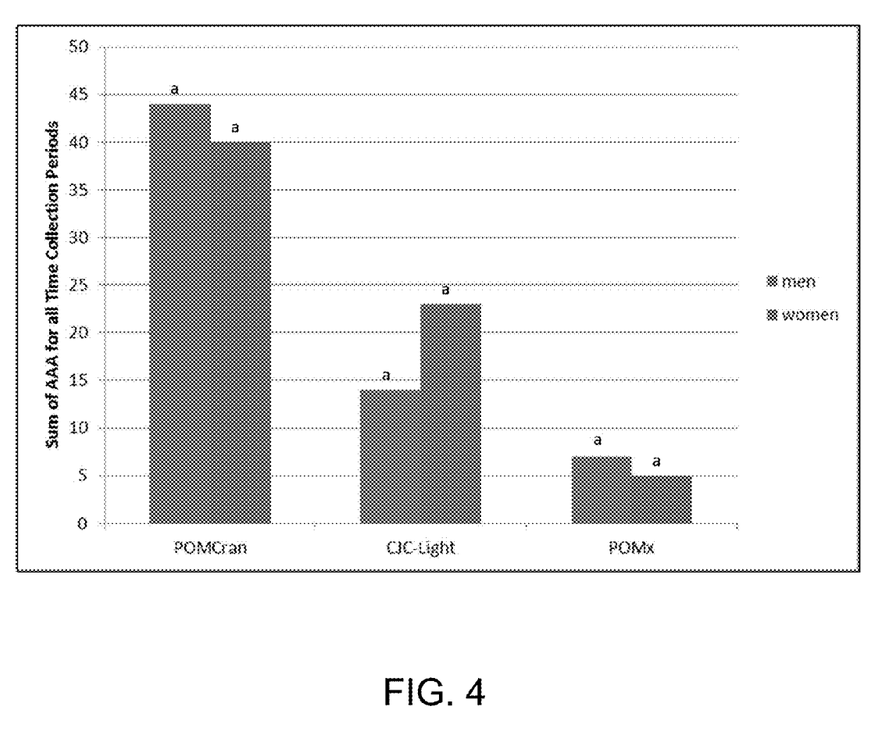
FIG. 4 is a graphical illustration of the overall product comparison of urinary P-type AAA against P-fimbriated *E. coli* by gender.

FIG. 4 is a graphical illustration of the overall product comparison of urinary P-type AAA against P-fimbriated E. coli by gender. As illustrated, there was no significant difference in AAA by gender following consumption of any of the products. Women and men both responded similarly to each product.

Analysis of POMCran Composition Components

Analysis of phenolics and tannins in POMCran juice components to try and understand any synergistic bacterial anti-adhesion effects of pomegranate and cranberry tannins when blended together were performed.

Tannins were isolated using the gravimetric technique. Reverse phase (C18) followed by adsorption chromatography (Sephadex LH-20) were used to fractionate and isolate the total tannins. An aqueous sample extract was loaded onto a C18 column, washed with water, then 15% methanol to elute off sugars and acids, followed by acidified methanol to elute the tannins. The tannin samples were dried, reconstituted in 50% methanol and loaded onto a Sephadex LH-20 column. The flavonols and anthocyanins were eluted with 50% methanol, followed by 70% acetone to recover the tannin fractions. The tannin elutions were lyophilized and weighed. Tannins were tested for AAA with a starting dilution of 6 mg/mL.

Results presented in Table 3 indicated that the cranberry concentrate has the highest AAA (a lower MIC value indicates greater anti-adhesion activity) as expected since this product contains the "A-type" proanthocyanidins that are known to inhibit the adherence of uropathogenic E. coli to uroepithelial cells. Pomegranate concentrate has very low activity in this assay and this result is in agreement with previous research on the AAA of pomegranate juice. However, the POMCran blend has greater AAA than expected from the proportion of cranberry (15%). From the results of the MIC for the pure concentrates we would expect an MIC value of >300 for POMCran if there was no interaction between the juice components in AAA. However, that was not the case thus suggesting an interaction or some form of synergy. In addition, the results from the MIC values for the isolated tannins is more suggestive of an interaction between the pomegranate ellagitannins and the cranberry "A-type" proanthocyanidins because POMCran tannin has a nearly identical MIC value to pure cranberry juice tannin, although mass spectrometry results indicate that the tannins in the blend are predominantly ellagitannins with only low levels of cranberry proanthocyanidins detected.

TABLE 3

Minimum concentration required to inhibit bacterial anti-adhesion activity (MIC) of pomegranate, cranberry and pomegranate cranberry blend (85:15) juice concentrates; isolated tannins from the concentrates; and amount of tannin extracted from each juice concentrate.

| Concentrate | MIC of Whole Concentrate (mg/mL) | MIC Isolated Tannins (mg/mL) | Tannin Weight (mg/mL) |
|---|---|---|---|
| POMCran | 40 | 0.0937 | 4 |
| Cranberry | 18.4 | 0.1875 | 12.6 |
| Pomegranate | 315-630 | 0.75 | 2.4 |

While the invention herein disclosed has been described by means of specific embodiments and applications thereof, numerous modifications and variations could be made thereto by those skilled in the art without departing from the scope of the invention set forth in the claims.

What is claimed is:

1. An oral dosage unit for treatment of urinary tract infection comprising:
   a capsule containing a composition consisting essentially of (1) a pomegranate extract that comprises hydrolyzable tannins and (2) a concentrated cranberry juice within said capsule, wherein:
   between about 50% to about 90% by weight of the composition is the pomegranate extract, wherein said pomegranate extract is obtained from pomegranate solids; and
   between about 10% to about 50% by weight of the composition is the concentrated cranberry juice, wherein said pomegranate extract and said concentrated cranberry juice combine to form a composition with a synergistic effect of increasing urinary tract anti-adhesion activity.

2. The oral dosage unit of claim 1, wherein the ratio of total polyphenolic content in said composition is approximately 85% from said pomegranate extract and approximately 15% from said concentrated cranberry juice.

3. The oral dosage unit of claim 1, wherein said concentrated cranberry juice is dehydrated cranberry juice.

4. The oral dosage unit of claim 1, wherein said pomegranate extract is powdered.

5. The oral dosage unit of claim 1, wherein the ratio of total polyphenolic content in said composition is approximately 80% from said pomegranate extract and approximately 20% from said concentrated cranberry juice.

6. The oral dosage unit of claim 1, wherein said capsule is a hard or soft shelled gelatin capsule.

7. An oral dosage unit for treatment of urinary tract infection comprising:
   a capsule;
   a composition within said capsule, wherein approximately 85% by weight of the composition is pomegranate juice concentrate, and approximately 15% by weight of the composition is cranberry juice concentrate, wherein said pomegranate juice concentrate and said cranberry juice concentrate combine to form a composition with a synergistic effect of significantly increasing urinary tract bacterial anti-adhesion activity.

8. The oral dosage unit of claim 7, wherein said pomegranate juice concentrate is dehydrated pomegranate juice.

9. The oral dosage unit of claim 7, wherein said cranberry juice concentrate is dehydrated cranberry juice.

10. The oral dosage unit of claim 7, wherein said capsule is a hard or soft shelled gelatin capsule, and said composition further contains comprises a suitable carrier or excipient.

11. The oral dosage unit of claim 7, wherein said pomegranate juice concentrate is dehydrated pomegranate juice and said cranberry juice concentrate is dehydrated cranberry juice.

12. The oral dosage unit of claim 11, wherein said capsule is a hard or soft shelled gelatin capsule, and said composition further comprises a suitable carrier or excipient.

* * * * *